United States Patent [19]

Moden et al.

[11] Patent Number: 5,013,298

[45] Date of Patent: May 7, 1991

[54] LATERALLY COMPRESSED SEPTUM ASSEMBLY AND IMPLANTABLE INFUSION PORT WITH LATERALLY COMPRESSED SEPTUM

[75] Inventors: James R. Moden, Bristol; Michael D. Caldwell, East Greenwich; Robert D. Moden, Warren, all of R.I.

[73] Assignee: Surgical Engineering Associates, Inc., Bristol, R.I.

[21] Appl. No.: 310,637

[22] Filed: Feb. 13, 1989

[51] Int. Cl.⁵ .......................................... A61M 11/00
[52] U.S. Cl. ..................................... 604/93; 604/175; 604/244; 604/86
[58] Field of Search ................ 604/132, 86, 175, 244, 604/93, 185

[56] References Cited

U.S. PATENT DOCUMENTS 4,762,517 8/1988 McIntyre et al. ................ 604/175
4,781,680 11/1988 Redmond et al. ................ 604/86 X

*Primary Examiner*—John D. Yasko
*Attorney, Agent, or Firm*—Salter & Michaelson

[57] ABSTRACT

A surgically implantable infusion port includes a housing portion, a penetrable elastomeric septum portion which cooperates with the housing portion for defining an interior cavity and a catheter element which extends outwardly from the interior cavity for dispensing medication therefrom at a predetermined location in the body of a patient. The elastomeric septum portion is penetrable by a hypodermic needle for dispensing medication in the interior cavity, and it is laterally compressed to enhance the ability of the septum portion to reseal itself after being repeatedly penetrated. A septum assembly including a similar laterally compressed septum element can also be utilized as a penetrable barrier between various liquids and gases.

8 Claims, 3 Drawing Sheets

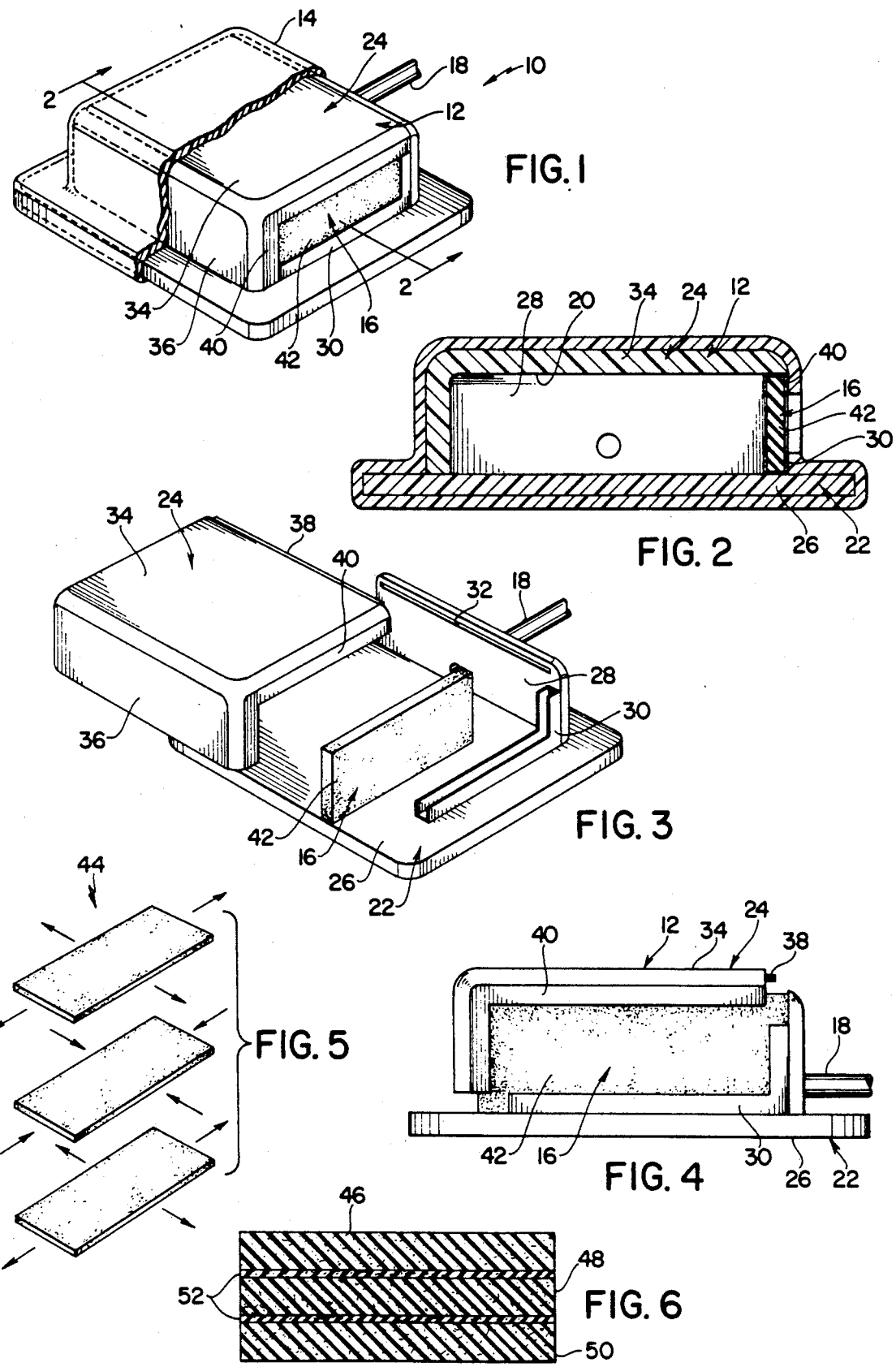

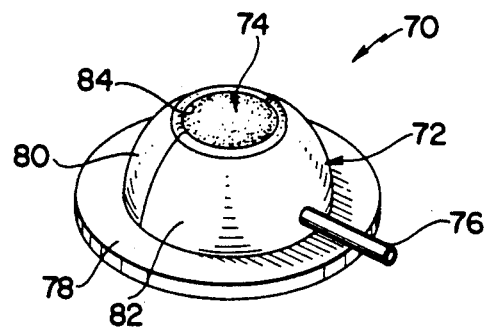
FIG. 9
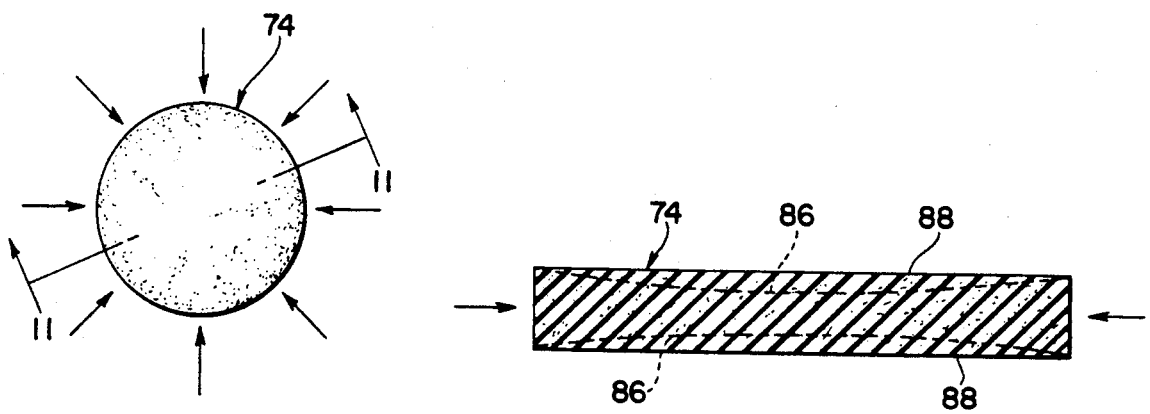
FIG. 10
FIG. 11

LATERALLY COMPRESSED SEPTUM ASSEMBLY AND IMPLANTABLE INFUSION PORT WITH LATERALLY COMPRESSED SEPTUM

BACKGROUND AND SUMMARY OF THE INVENTION

The instant invention relates to medical apparatus and more particularly to a self-sealing laterally compressed elastomeric septum which is penetrable by a hypodermic needle or the like and to a surgically implantable infusion port which includes the septum.

Surgically implantable infusion ports have been heretofore available for a number of years, and have generally been found to be effective for dispensing medication in the bodies of patients. One of the most common types of heretofore available infusion ports comprises a rubberized base portion, a metallic housing on the base portion having an interior cavity therein and an opening at the upper end thereof, a penetrable elastomeric septum which is received in sealing relation in the opening in the housing, and a catheter which extends from the interior cavity to the exterior of the housing. In use, an infusion port of this type is normally surgically implanted in a patient so that it is positioned beneath the skin with the upper end of the housing and the penetrable septum facing outwardly, and with the catheter positioned so that it can transmit medication to a predetermined area of the patient's body, such as a large vein. Once an infusion port of this type has been surgically implanted in the body of a patient, the cavity in the housing can be filled with medication by inserting a hypodermic needle through the skin of the patient so that the tip portion of the needle penetrates the septum and passes into the interior cavity and by then dispensing medication in the cavity through the needle. In most instances, after a predetermined amount of medication has been dispensed in this manner, the hypodermic needle is removed, so that the elastomeric septum reseals itself in the area where it was penetrated by the hypodermic needle. However, it has been found that each time the septum of an infusion port of this type is penetrated by a needle, a certain amount of damage is caused to the septum and that after a septum has been repeatedly penetrated, it can lose its ability to reseal itself. It has been further found that when this occurs, it is generally necessary to surgically replace the entire infusion port.

Another type of heretofore available infusion port is disclosed in the Moden et al U.S. Pat. No. 4,710,174. This device is intended to be utilized in a similar manner to that hereinabove set forth, although it is adapted for side entry with a hypodermic needle rather than top entry, such as with the above mentioned device.

The instant invention provides an effective septum which is laterally compressed to enhance the ability thereof to repeatedly reseal itself over a prolonged period of time and an effective infusion port which incorporates the septum. Specifically, the infusion port of the instant invention comprises a housing portion having an interior cavity therein and an access opening in the housing, a septum received in sealing relation in the access opening, and a catheter which extends between the interior cavity and the exterior of the housing for dispensing medication in the body of a patient. The septum of the instant invention is made of a substantially solid elastomeric material and it has an outwardly facing surface thereon. The septum is penetrable by a hypodermic needle by inserting the needle through the outwardly facing surface of the septum. The septum is compressed by between approximately 1% and 30% in a direction which is substantially parallel to the outwardly facing outer surface thereof, and it is preferably compressed by between 5% and 10% in two substantially perpendicular directions, both of which are parallel to the outwardly facing surface of the septum. In one embodiment of the infusion port, the septum is of substantially circular configuration and it is compressed in at least two radially extending directions. In this embodiment, the septum is preferably substantially flat, but it is preferably at least slightly concave prior to being compressed. In another embodiment, the septum comprises first and second layers of elastomeric material, wherein the first layer is operative for applying a compressive force to the second layer in order to maintain the second layer in a compressed disposition.

It has been found that because the infusion port of the instant invention includes a laterally compressed septum, it has an increased effective life as compared to many of the heretofore available infusion ports. Specifically, it has been found that the septum of the infusion port of the subject invention has a substantially increased ability to reseal itself after repeated penetration, and that as a result, the effective life of the septum is substantially increased. Accordingly, the infusion port of the instant invention can normally remain implanted in the body of a patient for an extended period of time before surgical replacement is necessary. It has also been found that the compressed septum of the instant invention can be effectively utilized in a variety of other applications to provide a resealable barrier between two fluids, including liquids and/or gases. For example, the compressed septum can be effectively utilized as a penetrable barrier for dispenser bottles of the type commonly utilized for filling hypodermic syringes.

Accordingly, it is a primary object of the instant invention to provide an effective infusion port having a laterally compressed septum.

Another object of the instant invention is to provide an infusion port comprising a septum having an enhanced ability to reseal itself after being repeatedly penetrated with a hypodermic needle.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a perspective view of a first embodiment of the infusion port of the instant invention;

FIG. 2 is a sectional view taken along line 2—2 in FIG. 1;

FIG. 3 is an exploded perspective view thereof;

FIG. 4 is an end elevational view thereof;

FIG. 5 is an exploded perspective view of a septum;

FIG. 6 is an enlarged sectional view of the septum;

FIG. 9 is a perspective view of a third embodiment of the infusion port;

FIG. 10 is a top plan view of the septum thereof; and

FIG. 11 is an enlarged sectional view taken along line 11—11 in FIG. 10.

DESCRIPTION OF THE INVENTION

Figure 7:
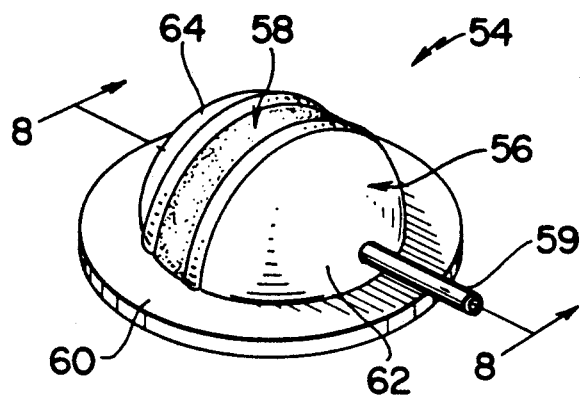
FIG. 7 is a perspective view of a second embodiment of the infusion port.

Referring now to the drawings, a first embodiment of the infusion port of the instant invention is illustrated in FIGS. 1-4 and generally indicated at 10. The infusion port 10 is adapted to be surgically implanted in the body of a patient for dispensing medication therein, and it comprises a housing generally indicated at 12, an outer casing 14 on the housing 12, a septum 16, and a catheter 18. The septum 16 is received in sealing relation in an access opening in the housing 12 so that it cooperates with the housing 12 to define an interior cavity 20, and the casing 14 provides a cushioned outer casing on the housing 12 in order to reduce patient discomfort. The catheter element 18 is assembled with the housing 12 so that it communicates with the cavity 20, and it extends outwardly from the housing 12 for dispensing medication at a predetermined location in the body of the patient. The septum 16 is adapted to be penetrated by a hypodermic needle in order to introduce medication into the cavity 20 so that the medication can be dispensed at the desired location in the body of the patient through the catheter element 18.

The housing 12 comprises first and second housing sections generally indicated at 22 and 24, respectively, which are preferably made of a suitable plastic material and receivable in assembled relation to define the housing 12. The first housing section 22 includes a bottom wall 26, an apertured, upstanding first sidewall 28 on the bottom wall 26, and an angled channel member 30 which extends along the bottom wall 26 and then upwardly along the inner side of the first sidewall 28. An elongated slot 32 is formed along the upper edge of the first sidewall 28. The second housing section 24 comprises a top wall 34, a second sidewall 36, which depends from the top wall 34, and a third sidewall (not shown) which also depends from the top wall 34. An elongated tongue 38 is formed along one edge of the top wall 34, and an angled channel member 40 extends along the underside of the top wall 34 at the end thereof opposite the third sidewall (not shown), and then downwardly along the inner side of the second sidewall 36. The first and second housing sections 22 and 24 are receivable in assembled relation so that the tongue 38 is received in the groove 32 and so that the housing sections 22 and 24 cooperate to define the housing 12. When the housing sections 22 and 24 are assembled in this manner, the channel members 30 and 40 cooperate to define an opening for receiving the septum 16 and for maintaining it in a laterally compressed disposition.

The septum 16 is preferably made of a nontoxic, solid, elastomeric material, such as a silicone rubber, having a Shore A durometer of between 30 and 90 (preferably between 40 and 70). The septum 16 is of substantially flat, rectangular configuration, and it includes a substantially flat outwardly facing outer surface 42. The septum 16 is assembled between the first and second housing sections 22 and 24, respectively, so that it is received in the channel members 30 and 40 thereof, respectively. In this connection, as illustrated in FIG. 4, the septum 16 is dimensioned so that as it is assembled between the first and second housing sections 22 and 24, respectively, it is compressed in both a first direction which is substantially parallel to the surface 42 and extends between the first and second sidewalls 28 and 36, and a second direction which is substantially parallel to the surface 42 and extends between the top and bottom walls 34 and 26, respectively. The septum 16 is dimensioned so that it is compressed by between 1% and 30% (preferably between 5% and 10%) as the housing sections 22 and 24 are assembled together.

The catheter element 18 is preferably made of a suitable nontoxic, elastomeric material, such as a silicone rubber, and it is attached to the first sidewall 28 so that it communicates with the cavity 20 and extends outwardly from the housing 12 for dispensing medication in the body of a patient.

The casing 14 is preferably also made of a suitable silicone rubber, and it extends over all of the outer surfaces of the housing 12 to provide a cushioned outer covering therefor in order to reduce patient discomfort.

In use, the infusion port 10 is surgically implanted in the body of a patient, and the catheter element 18 is positioned so that it can be utilized for dispensing medication in a predetermined area of the patient's body, such as in a large vein. Thereafter, medication can be introduced into the infusion port 10 by inserting a hypodermic needle through the adjacent area of the patient's skin so that the tip of the needle passes through the septum 16 and into the cavity 20. Once the desired amount of medication has been dispensed in the cavity 20, the hypodermic needle can be withdrawn from the septum 16 and removed from the patient. In this regard, because the septum 16 is laterally compressed, it is able to effectively reseal itself after being repeatedly punctured so that the infusion port 10 has a substantially increased effective life.

A precompressed septum assembly which can be alternatively utilized in an infusion port, such as the infusion port 10, is illustrated in FIGS. 5 and 6 and generally indicated at 44. The septum assembly 44 comprises a first compression layer 46, a septum layer 48 and a second compression layer 50, all of which are made from a suitable solid, elastomeric material, such as silicone rubber having a durometer of between 30 and 90. The compression layers 46 and 50 are secured to the septum layer 48 with adhesive layers 52 comprising a suitably known adhesive. However, during assembly of the first and second compression layers 46 and 50 with the septum layer 48, the compression layers 46 and 50 are longitudinally and transversely stretched in directions which are substantially parallel to the main planar surfaces thereof, whereas the septum layer 48 is preferably but not necessarily both longitudinally and transversely compressed in directions which are substantially parallel to the main planar surfaces thereof. Accordingly, after the first and second layers 46, and 50 have been secured to the septum layer 48 with the adhesive 52, the first and second compression layers 46 and 50 cooperate to apply compressive forces to the septum layer 48. In this connection, once the septum assembly 44 has been formed in this manner, the septum layer 48 is normally maintained in a disposition wherein it is compressed by between 1% and 30% (preferably between 5% and 10%). Thereafter, the septum assembly 44 can be assembled in an infusion port in a manner which does not require additional compression.

Figure 8:
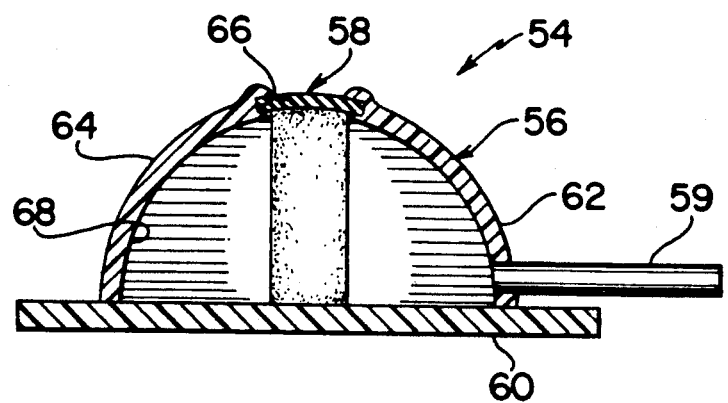
FIG. 8 is an enlarged sectional view taken along line 8—8 in FIG. 7.

A second embodiment of the infusion port of the instant invention is illustrated in FIGS. 7 and 8, and generally indicated at 54. The infusion port 54 comprises a housing generally indicated at 56, a septum generally indicated at 58, and a catheter element 59. The housing 56 comprises a substantially flat, base portion 60 and a split dome-shaped portion comprising a pair of dome sections 62 and 64. The dome sections 62 and 64 are preferably made of a suitable plastic material and they are received on the base portion 60 so that they cooperate to define an elongated arcuate opening therebetween for containing the septum 58. In this connection, channels 66 are formed in the opposed edges of the dome sections 62 and 64 for receiving and containing the septum 58 so that it cooperates with the housing 56 for defining an interior cavity 68. The septum 58 is preferably also made of a solid elastomeric material having a durometer of between 30 and 90 (preferably between 40 and 70), and it is dimensioned so that when it is received in the channels 66 it is compressed in a direction which extends between the dome sections 62 and 64, i.e., in a lateral direction which is substantially parallel to the outer surface of the septum 58. The septum 58 is compressed by between 1% and 30% and preferably by between 5% and 10% when it is assembled between the dome sections 62 and 64. The catheter element 59 is secured to the dome section 62 so that it communicates with the interior cavity 68 and it extends outwardly from the housing 56 for dispensing medication in the body of a patient.

In use, the infusion port 54 is surgically implanted in the body of a patient so that the catheter element 59 is properly positioned to dispense medication at a predetermined location in the body. Thereafter, medication can be introduced into the cavity 68 by passing a hypodermic needle through the adjacent area of the patient's skin and through the septum 58. When the hypodermic needle is thereafter removed, the laterally compressed septum 58 is able to effectively reseal itself so that it can be repeatedly punctured over a prolonged period of time.

A third embodiment of the infusion port of the instant invention is illustrated in FIGS. 9-11, and generally indicated at 70 in FIG. 9. The infusion port 70 comprises a housing generally indicated at 72, a septum generally indicated at 74, and a catheter element 76. The housing 72 and the septum 74 cooperate to define an interior cavity for receiving medication therein, and the catheter element 76 communicates with the cavity for dispensing medication therefrom at a predetermined location in the body of a patient.

The housing 72 is preferably made of a suitable plastic material or a metal, and it comprises a substantially flat, circular base portion 78 and a pair of dome sections 80 and 82 which cooperate to define a rounded dome having a substantially circular opening 84 at the upper end thereof. The upper extremities of the dome sections 80 and 82 define an inwardly facing circular channel (not shown) for receiving and containing the septum 74. The septum 74 is of substantially circular configuration, and it is made of an elastomeric material, such as silicone rubber, having a Shore A durometer of between 30 and 90 (preferably between 40 and 70). As illustrated schematically in FIG. 10, the septum 74 is compressed in a plurality of radial directions. In this connection, the septum 74 is compressed by between 1% and 30% (preferably between 5% and 10%), and it is maintained in a compressed disposition by the dome sections 80 and 82. As illustrated in FIG. 11, the septum 74 is preferably formed so that before it is placed under compression, its side faces are at least slightly concave as indicated by the dotted lines 86, and it is compressed so that it is deformed to the point where its opposite side faces are substantially flat and parallel as indicated by the solid lines 88. As a result, the entire septum 74 can be effectively maintained in a compressed disposition without causing any portions thereof to be placed under tension due to distortion. The catheter element 76 is preferably made of a suitable elastomeric material, such as silicone rubber, and it is received in the dome section 82 so that it extends outwardly therefrom for dispensing medication from the interior cavity defined by the housing 72 and the septum 74.

The infusion port 70 is also adapted to be installed in the body of a patient in the manner hereinabove set forth with respect to the infusion ports 10 and 54. Further, because the septum 74 is maintained in a compressed state, it is effectively able to reseal itself each time it is punctured by a hypodermic needle so that the infusion port 70 can remain in the body of a patient over a prolonged period of time.

It is seen therefore that the instant invention provides an effective infusion port for dispensing medication in the body of a patient. The septa 16, 58 and 74 of the infusion ports 10, 54 and 70, respectively, and the septum 44 are all maintained under sufficient compression to enable them to effectively reseal themselves after they have been repeatedly penetrated by hypodermic needles. As a result, the septa 16, 44, 58 and 74 have extended effective life cycles so that infusion ports in which they are installed can remain implanted in the bodies of patients for extended periods of time. Hence, for these reasons, it is seen that the instant invention represents a significant advancement which has substantial merit in the medical art.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. In an implantable infusion port for dispensing medication in the body of a patient including a housing having an access opening therein, a septum made of a substantially solid elastomeric material received in said access opening and cooperating with said housing for defining a substantially closed interior cavity, said septum having an outwardly lacing outer surface thereon and being penetrable by a hypodermic needle by inserting said needle through said outwardly facing surface, and catheter means communicating with said cavity for dispensing medication therefrom into the body of said patient, the improvement comprising said septum having an inwardly facing surface which faces substantially opposite from said outwardly facing surface, said infusion port further comprising first and second elastomeric layers secured in overlying relation on said outwardly facing surface and said inwardly facing surface, respectively, said first and second compression layers cooperating to compress said septum by between 1% and 30% in a direction which is substantially parallel to said outwardly and inwardly facing surfaces.

2. In an implantable infusion port for dispensing medication in the body of a patient including a housing having an access opening therein, a septum made of a substantially solid elastomeric material received in said access opening and cooperating with said housing for defining a substantially closed interior cavity, said septum having opposite outwardly and inwardly facing surfaces and being penetrable by a hypodermic needle by inserting said needle through said outwardly facing surface, and catheter means communicating with said cavity for dispensing medication therefrom into the body of said patient, the improvement comprising said outwardly and inwardly facing surfaces being substantially parallel, said septum being compressed by between 1% and 30% in at least first and second substantially perpendicular directions which are substantially parallel to said outwardly and inwardly facing surfaces, said septum being formed so that each of said outwardly and inwardly facing surfaces is at least slightly concave prior to compressing said septum in said first and second directions.

3. In the infusion portion of claim 2, said septum being compressed by between 1% and 30% in each of said first and second substantially perpendicular directions.

4. In the infusion port of claim 3, said septum being compressed by between 5% and 10% in each of said first and second directions.

5. A precompressed septum assembly comprising an elastomeric septum layer having substantially parallel opposite first and second surfaces and first and second elastomeric compression layers secured in overlying relation on said first and second surfaces, respectively, said septum layer and said first and second compression layers being penetrable by a hypodermic needle, said first and second compression layers cooperating to compress said septum layer by between 1% and 30% in a direction substantially parallel to said first and second surfaces.

6. In the septum assembly of claim 5, said first and second compression layers cooperating to compress said septum layer by between 1% and 30% in two perpendicular directions which are substantially parallel to said first and second surfaces.

7. A precompressed septum assembly comprising an elastomeric septum layer having opposite substantially parallel first and second surfaces and an elastomeric compression layer secured in overlying relation on the first surface of said septum layer, said septum layer and said compression layer being penetrable by a hypodermic needle, said compression layer maintaining said septum layer in a disposition wherein it is compressed by between 1% and 30% in a direction substantially parallel to said first and second surfaces.

8. In an implantable infusion port for dispensing medication in the body of a patient including a housing having an access opening therein, a septum made of a substantially solid elastomeric material received in said access opening and cooperating with said housing for defining a substantially closed interior cavity, said septum having opposite outwardly and inwardly facing surfaces and being penetrable by a hypodermic needle by inserting said needle through said outwardly facing surface, and catheter means communicating with said cavity for dispensing medication therefrom into the body of said patient, the improvement comprising said housing including a shell portion of rounded dome-like configuration and a substantially flat base portion, said shell portion including first and second shell portion sections which cooperate to substantially define said shell portion, said first and second shell portion sections being received on said base portion and cooperating therewith to define said interior cavity, said first and second shell portion sections cooperating to define said access opening and cooperating to compress said septum in said access opening by between 1% and 30% in a direction substantially parallel to said outwardly facing surface, said access opening being in the configuration of an arcuate band extending across said dome-like shell portion.

* * * * *